United States Patent [19]

Yanaihara

[11] 4,407,965
[45] Oct. 4, 1983

[54] PROCESS FOR PREPARING ANTIBODY

[75] Inventor: Noboru Yanaihara, Shizuoka, Japan

[73] Assignee: Otsuka Pharmaceutical Co., Ltd., Tokyo, Japan

[21] Appl. No.: 265,926

[22] Filed: May 21, 1981

[30] Foreign Application Priority Data

May 21, 1980 [JP] Japan .................................. 55-68040

[51] Int. Cl.³ ...................... C07G 7/00; C07C 103/52; G01N 23/00; G01N 33/00
[52] U.S. Cl. .................................... 436/547; 424/85; 260/112 B; 260/112.5 R; 260/112 R; 436/822; 436/823
[58] Field of Search .................................. 424/85, 88; 260/112.5 R, 112 B; 436/547

[56] References Cited

U.S. PATENT DOCUMENTS 4,206,199 6/1980 Fujino et al. .......................... 424/85
4,221,777 9/1980 Nishino ................................ 424/85

OTHER PUBLICATIONS

Chemical Abstracts, vol. 93, pp. 102, 696, 1028, Abst. Nos. 161615g, 132782m, 72244a, 1980.

Primary Examiner—Blondel Hazel
Attorney, Agent, or Firm—Sughrue, Mion, Zinn, Macpeak, and Seas

[57] ABSTRACT

A process for preparing a gut glucagon antigen composed of a peptide-carrier complex is disclosed, which comprises using as hapten a peptide represented by the following general formula;

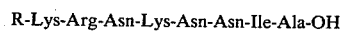

R-Lys-Arg-Asn-Lys-Asn-Asn-Ile-Ala-OH wherein R represents a hydrogen atom, an amino acid group or a peptide group containing 2 to 20 amino acid groups, and reacting it with a carrier in the presence of a binding agent for binding the hapten and the carrier to each other. Also, a process for preparing a gut glucagon antibody, which comprises administering the antigen described to mammals, and collecting the thus-produced antibody, is disclosed.

8 Claims, 4 Drawing Figures

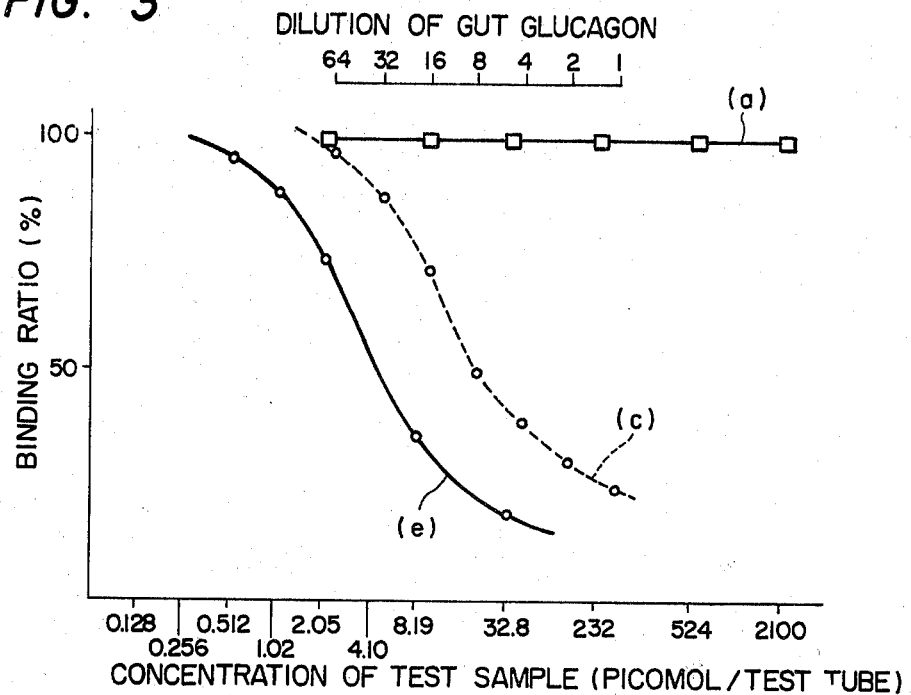
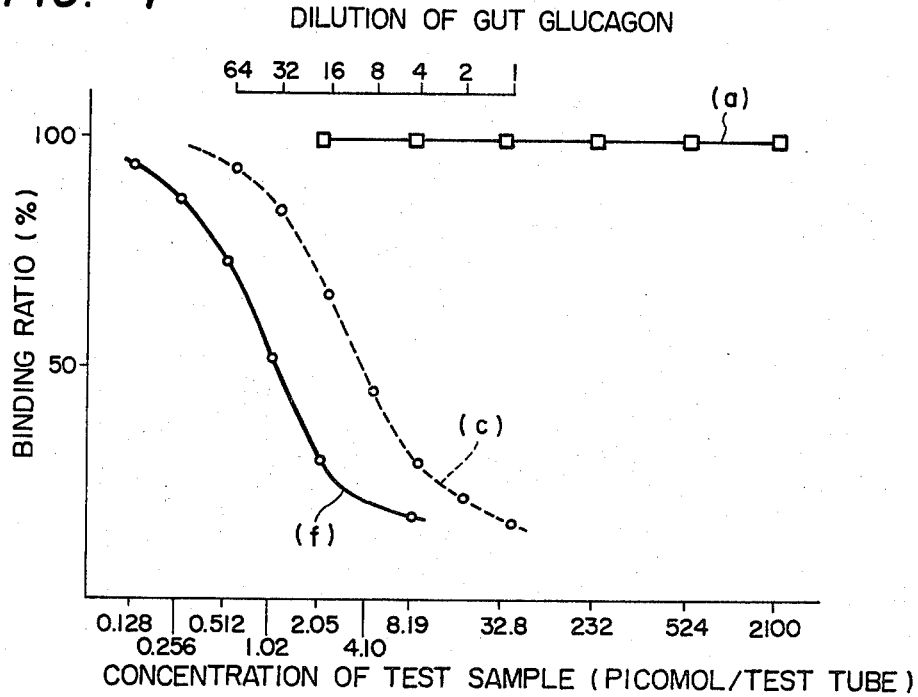

PROCESS FOR PREPARING ANTIBODY

BACKGROUND OF THE INVENTION

This invention relates to a process for preparing a gut glucagon antigen.

In this specification, abbreviations for various amino acids, peptides, protective groups, active groups, etc. are given by following the rules of IUPAC or IUB or by using conventional symbols, examples of which are shown below. And, where amino acids can include optical isomers, they are intended to indicate L-enantiomers unless otherwise specified.

Arg: arginine
Trp: tryptophane
Asn: asparagine
Asp: aspartic acid
Thr: threonine
Ser: serine
Glu: glutamic acid
Gln: glutamine
Ala: alanine
Val: valine
Met: methionine
Leu: leucine
Phe: phenylalanine
Lys: lysine
Tyr: tyrosine
Ile: isoleucine
Cys: cysteine $$\begin{matrix} Cys \\ | \\ Cys \end{matrix} : \text{cystine}$$

Gly: glycine
His: histidine
Pro: proline
Z: carbobenzoxy group
Su: succinimido group
Tos: p-toluenesulfonyl group
Boc: tert-butoxycarbonyl group Gut glucagon is a hormone playing an important role in sugar absorption metabolism. Assay of gut glucagon enables one to diagnose various pathological states gut glucagon takes part in, such as diabetes mellitus or gut cancer, and diagnose diseases such as gut diseases (e.g., diarrhoea, constipation, etc.), duodendal ulcer, carcinoid, gut glucagonoma, etc. Thus, assay of gut glucagon is increasingly noted in the field of diagnosis, pathology, physiology, etc. Gut glucagon is assayed by a method such as a radioimmunoassay method (RIA method) using an antibody (antiserum) which reacts with gut glucagon. As the antibody capable of reacting with gut glucagon, there has so far been known antibody R-64 prepared by Ravazzola et al [see *Endocrinology*, vol. 105, No. 2, pp. 499-508 (1979)]. However, such antibody does not have a specificity to gut glucagon.

SUMMARY OF THE INVENTION

With the above-described present situation in mind, extensive investigations have been made to develop a process for obtaining an antibody having specificity to gut glucagon and being extremely effective for assaying gut glucagon according to RIA method or the like and, in the course of the investigation, it has been discovered that the 93-100 N-terminal peptide sequence of porcine glicentin [see *Horm. Metab. Res.*, 8, 366-371 (1976)], i.e., H-Lys-Arg-Asn-Lys-Asn-Asn-Ile-Ala-OH is an antigen determinant of an antibody having specificity to gut glucagon. As a result of further investigation based on the novel findings described above, an antigen comprising as hapten a peptide containing the specific peptide sequence described above and represented by the general formula (1) given hereinafter has been synthesized successfully, and from this antigen an intended excellent antibody having high specificity to gut glucagon has been prepared. Thus the present invention has been completed.

That is, the present invention provides a process for preparing a gut glucagon antigen comprising a peptide-carrier complex, which comprises using as hapten a peptide represented by the following general formula (1);

R-Lys-Arg-Asn-Lys-Asn-Asn-Ile-Ala-OH        (1)

wherein R represents a hydrogen atom, an amino acid group or a peptide group containing 2 to 20 amino acid groups, and reacting it with a carrier in the presence of a binding agent for binding the hapten and the carrier to each other, and a process for preparing an antibody using said antigen.

BRIEF DESCRIPTION OF THE DRAWINGS

FIGS. 1 through 4 are graphs showing specificity of antibodies of the present invention.

DETAILED DESCRIPTION OF THE INVENTION

Figure 1:
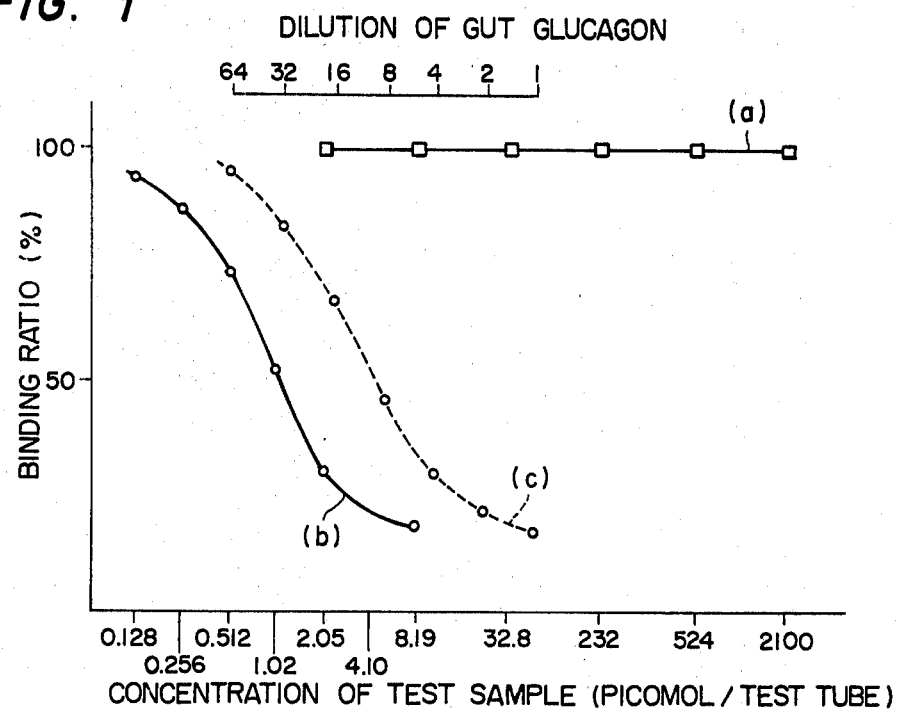

In the process of the present invention, it is indispensable to use as hapten a peptide represented by the general formula (1) given above. As the amino acid group represented by R in the general formula (1), there are illustrated, for example, H-Arg-, H-Trp-, H-Asn-, H-Ala-, H-Val-, H-Met-, H-Leu-, H-Phe-, H-Lys-, H-Tyr-, H-Ile-,

H-Gly-, H-His-, H-Pro, H-Cys, etc.

As the peptide group containing 2 to 20 amino acid groups, there are illustrated, for example, H-Gly-Lys-, H-Asn-Tyr-, H-Met-Thr-, H-Met-Asn-, H-Leu-Thr-, H-Trp-Thr-, H-Phe-Val-, H-Gln-Ala-, H-Asp-Arg-, H-Leu-Tyr-, H-Ser-Lys-, H-Met-Asn-Thr-, H-Leu-Met-Asn-Thr-, H-Trp-Leu-Met-Asn-Thr-, H-Gln-Trp-Leu-Met-Asn-Thr-, H-Val-Gln-Trp-Leu-Met-Asn-Thr-, H-Phe-Val-Gln-Trp-Leu-Met-Asn-Thr-, H-Asp-Phe-Val-Gln-Trp-Leu-Met-Asn-Thr-, H-Gln-Asp-Phe-Val-Gln-Trp-Leu-Met-Asn-Thr-, H-Ala-Gln-Asp-Phe-Val-Gln-Trp-Leu-Met-Asn-Thr-, H-Arg-Ala-Gln-Asp-Phe-Val-Gln-Trp-Leu-Met-Asn-Thr-, H-Arg-Arg-Ala-Gln-Asp-Phe-Val-Gln-Trp-Leu-Met-Asn-Thr-, H-Ser-Arg-Arg-Ala-Gln-Asp-Phe-Val-Gln-Trp-Leu-Met-Asn-Thr-, H-Asp-Ser-Arg-Arg-Ala-Gln-Asp-Phe-Val-Gln-Trp-Leu-Met-Asn-Thr-, H-Leu-Asp-Ser-Arg-Arg-Ala-Gln-Asp-Phe-Val-Gln-Trp-Leu-Met-Asn-Thr-, H-Tyr-Leu-Asp-Ser-Arg-Arg-Ala-Gln-Asp-Phe-Val-Gln-Trp-Leu-Met-Asn-Thr-, H-Lys-Tyr-Leu-Asp-Ser-Arg-Arg-Ala-Gln-Asp-Phe-Val-Gln-Trp-Leu-Met-Asn-Thr-, H-Ser-Lys-Tyr-Leu-Asp-Ser-Arg-Arg-Ala-Glu-Asp-Phe-Val-Gln-Trp-Leu-Met-Asn-Thr-.

Of these, peptides wherein R represents a peptide group or amino acid group formed by successively removing 1 to 19 amino acid groups from the N-terminus of the 73-92 N-terminal sequence of porcine glicentin are preferred.

As the carrier to be bound to the hapten, there can be used a wide variety of high molecular natural or synthetic proteins conventionally used for preparing antigens. For example, there are illustrated animal serum albumins (e.g., equine serum albumin, bovine serum albumin, rabbit serum albumin, human serum albumin, sheep serum albumin, etc.), animal serum globulins (e.g., equine serum globulin, bovine serum globulin, rabbit serum globulin, human serum globulin, sheep serum globulin, etc.), thyroglobulins of animals (e.g., equine thyroglobulin, bovine thyroglobulin, rabbit thyroglobulin, human thyroglobulin, sheep thyroglobulin, etc.), hemoglobins of animals (e.g., equine hemoglobin, bovine hemoglobin, rabbit hemoglobin, human hemoglobin, sheet hemoglobin, etc.), hemocyanines of animals, protein extract from ascaris (Ascaris extract; see Japanese patent application (OPI) No. 16414/81), polylysine, polyglutamic acid, lysine-glutamic acid copolymer, lysine- or ornithine-containing copolymer, etc.

The Ascaris extract will be described in detail below. The Ascaris extract is obtained by extracting Ascaris suum grinds according to an ordinary protein-extracting process. As an extracting solvent, there can be used various known protein-extracting solvents such as water, a physiological saline solution, a 50% methanol or ethanol aqueous solution, an approximately neutral buffer solution, etc., with physiological saline solution being preferred. More specifically, the above-described extract is obtained, for example, as follows. That is, viscerafree Ascaris suum is washed with a physiological saline solution and, preferably, cut into fine pieces to facilitate the extraction. Then, the fine pieces are added to a protein-extracting solvent such as a physiological saline solution followed by extracting while homogenizing the mixture. This extraction is usually conducted at low temperatures, preferably at about 2° to 10° C. The thus obtained extraction solution is then centrifuged, and the supernatant is collected. After dialysis of the supernatant, the dialysate is lyophilized. Or else, said dialysate is again centrifuged, the supernatant is collected and, after removal of suspended matter, lyophilized. Thus, the intended Ascaris extract is prepared. This can be utilized in the present invention, if necessary, after further purifying according to ordinary protein-purifying means such as a dialysis method, gel filtration method, adsorption method, chromatography, etc. Ascaris extracts described in, for example, *J. Immun.*, 111, 260–268 (1973), *J. Immun.*, 122, 302–308 (1979), *J. Immun.*, 98, 893–900 (1967) and *Am. J. Physiol.*, 199, 575–578 (1960) or those prepared by further purifying these extracts may also be used in the present invention.

As the binding agent for binding the hapten and the carrier to each other, those which are conventionally used in preparing antigens can widely be used. Specifically, there are illustrated aliphatic dialdehydes capable of crosslinking amino groups to each other such as glyoxal, malondialdehyde, glutaraldehyde, succinaldehyde, adipoaldehyde, etc.; dimaleimides capable of crosslinking thiol groups to each other such as N,N'-o-phenylenedimaleimide, N,N'-m-phenylenedimaleimide, etc.; maleimidocarboxyl-N-hydroxysuccinimide ester compounds capable of crosslinking amino group to thiol group such as m-maleimidobenzoyl-N-hydroxysuccinimide ester, 4-(maleimidomethyl)-cyclohexane-1-carboxyl-N'-hydroxysuccinimide ester, etc.; reagents for use in ordinary peptide bond-forming reaction capable of linking amino group to carboxyl group through an amido bond such as dehydrate-condensing agents of carbodiimides (e.g., N,N-dicyclohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimide, etc.); and the like. Further, a combination of a diazoniumarylcarboxylic acid (e.g., p-diazoniumphenylacetic acid) and an ordinary peptide bond-forming reagent (e.g., the dehydrate-condensing agent described above) can also be used.

The antigen of the present invention is prepared by reacting the above-described hapten with the carrier in the presence of the binding agent for binding the hapten and the carrier to each other. This reaction is carried out in an aqueous solution or an ordinary buffer solution of 7 to 10, preferably 8 to 9, in pH at 0° to 40° C., preferably about room temperature. This reaction goes to completion in about 1 to 24 hours.

As the typical examples of the buffer to be used in this reaction, there are illustrated the following:

0.2 N sodium hydroxide-0.2 M boric acid-0.2 M potassium chloride buffer;

0.2 M sodium carbonate-0.2 M boric acid-0.2 M potassium chloride buffer;

0.05 M sodium tetraborate-0.2 M boric acid-0.05 M sodium chloride buffer; and 0.1 M sodium dihydrogenphosphate-0.05 M sodium tetraborate buffer.

In the above-described reaction, the proportion of hapten, binding agent and carrier may properly be determined. Usually, however, a preferred proportion by weight of carrier to hapten is 2:1 to 6:1, more preferably 3:1 to 5:1, and a preferred molar proportion of binding agent to hapten is 5:1 to 10:1. The above-described reaction provides a gut glucagon antigen of the present invention composed of the peptide-carrier complex wherein the carrier and the hapten are bound to each other via the binding agent for binding the hapten and the carrier to each other. The antigen formed by the reaction can easily be isolated and purified in a conventional manner by, for example, a dialysis method, a gel filtration method, a fractional precipitation method, or the like. The resulting antigen can be stored by lyophilizing in a conventional manner. In the thus-obtained antigens of the present invention, usually 5 to 20 moles, on the average, of the peptide is bound to 1 mole of the protein. Every such antigen enables to prepare an antibody having high specificity to gut glucagon with good reproducibility. In particular, antigens having a molar binding ratio of peptide to protein of 1:8 to 1:15 have higher specificity and enables to prepare an antibody with high activity and high sensitivity, thus being preferable.

Of the peptides of the general formula (1) to be used in the present invention some are known and others are novel compounds, which can be prepared by the processes described below.

The peptide of the general formula (1) can be prepared according to a conventional manner for synthesizing peptides. Either of solid phase processes and liquid phase processes may be employed, with the latter being advantageous in many cases. Such processes for synthesizing peptides are described in, for example, "The Peptides," vol. 1 (1966) written by Schröder and Luhke (Academic Press, New York, U.S.A.) or "Peptide Synthesis" written by Izumiya et al [Maruzen Co., Ltd. (1975)], and there are illustrated, for example, an azide process, a chloride process, an acid anhydride process, a mixed acid anhydride process, a DCC process, an active ester process, a process of using Woodward reagent K, a carbodiimidazole process, an oxidation-reduction process, a DCC/additive (e.g., HONB, HOBt, HOSu, etc.) process, and the like.

The peptide of the general formula (1) can be easily synthesized according to a process for synthesizing general polypeptides, for example, a so-called stepwise process of condensing amino acids one by one to the terminal amino acid or a process of coupling several fragments. More specifically, the above-described peptide can be prepared by condensing a reactive carboxyl group-containing starting material corresponding to one of the two fragments formed by separating the peptide at an arbitrary bond position with another reactive amino group-containing starting material corresponding to the other fragment in a manner conventionally employed for synthesis of peptides and, where the resulting condensate contains a protective group or groups, removing the protective group(s) in a conventional manner.

In the reaction steps for preparing the peptide of the general formula (1), aspartic acid is desirably protected in many cases and, in the final step, all protective groups are removed from the protected peptide containing at least one protected amino acid residue to prepare the intended peptide.

Protection of functional groups which should not participate in the reaction, protective groups, removal of the protective groups, and activation of functional groups participating in the reaction can be properly conducted in a conventional manner or selected from known ones.

As the protective group for the amino group of a starting material, there are illustrated, for example, carbobenzoxy, tert-butyloxycarbonyl, tert-amyloxycarbonyl, isobornyloxycarbonyl, p-methoxybenzyloxycarbonyl, 2-chlorobenzyloxycarbonyl, adamantyloxycarbonyl, trifluoroacetyl, phthalyl, formyl, o-nitrophenylsulphenyl, diphenylphosphinothioyl, etc. As the protective group for the carboxyl group, there are illustrated, for example, an alkyl ester group (e.g., methyl ester, ethyl ester, propyl ester, butyl ester, tert-butyl ester, etc.), a benzyl ester, a p-nitrobenzyl ester, p-methoxybenzyl ester, p-chlorobenzyl ester, a benzhydryl ester, a carbobenzoxyhydrazido group, tert-butyloxycarbonylhydrazido group, a tritylhydrazido group, etc.

As the protective group for the guanidino group of arginine, there are illustrated, for example, a nitro group, a tosyl group, a p-methoxybenzenesulfonyl group, a carbobenzoxy group, an isobornyloxycarbonyl group, an adamantyloxycarbonyl group, etc. The guanidino group may also be protected in the form of a salt with an acid (e.g., benzenesulfonic acid, toluenesulfonic acid, hydrochloric acid, sulfuric acid, etc.).

The hydroxy group of threonine can be protected by esterification or etherification. As the group suited for the esterification, there are illustrated, for example, lower alkanoyl groups (e.g., acetyl group, etc.), aroyl groups (e.g., benzoyl group, etc.), carbonic acid-derived groups (e.g., benzoyloxycarbonyl group, ethyloxycarbonyl group, etc.), and the like and, as the group suited for the etherification, there are illustrated, for example, a benzyl group, a tetrahydropyranyl group, a tert-butyl group, etc. However, the hydroxy group of threonine is not necessarily protected. Methionine may be protected in the form of sulfoxide.

As the examples of activated carboxyl group in the starting material, there are illustrated, for example, acid anhydrides, azides, active esters (esters with pentachlorophenol, p-nitrophenol, N-hydroxysuccinimide, N-hydroxybenzotriazole, N-hydroxy-5-norbornene-2,3-dicarboximide, etc.), and the like.

The peptide bond-forming reaction is in some cases conducted in the presence of a dehydrating agent such as a carbodiimide reagent (e.g., dicyclohexylcarbodiimide or carbodiimidazole).

The peptide bond-forming reaction can be conducted in the presence of a solvent. As such solvent, proper one can be selected from those which are known to be usable for peptide condensation reaction. Examples thereof include anhydrous or aqueous dimethylformamide, dimethylsulfoxide, pyridine, chloroform, dioxane, dichloromethane, tetrahydrofuran, ethyl acetate, N-methylpyrrolidone, and the mixtures thereof.

The reaction temperature is properly selected from the range known to be employable for peptide bond-forming reaction, usually from about $-40°$ to about $60°$ C., preferably from about $-20°$ C. to about $0°$ C.

After completion of the above-described condensation reaction, protective groups (if any) in the product can be removed in a conventional manner. As such conventional manner, there are illustrated, for example, a reducing process (for example, hydrogenation using a catalyst like palladium black, reduction using sodium metal in liquid ammonia, etc.), acidolysis (for example, acidolysis with a strong acid such as rifluoroacetic acid, hydrogen fluoride or methanesulfonic acid).

The peptide of the general formula (1) as described above is isolated from the reaction mixture and purified by a peptide-separating means such as extraction, distribution, column chromatography, etc.

A labelled peptide which is a starting material for producing a labelled antigen to be used in RIA method is prepaed by introducing radioactive iodine such as $^{125}I$ or $^{131}I$ into the above-prepared peptide. Introduction of the radioactive iodine is conducted by an ordinary iodination process, for example, an oxidative iodination process using chloramine T [see W. M. Hunter & F. C. Greenwood; Nature, 194, 495 (1962), Biochem. J., 89, 114 (1963)]. For example, this iodination process is conducted in a suitable solvent such as a 0.2 M phosphate buffer solution (pH=7.4) in the presence of chloramine T at about room temperature for 10 to 30 seconds. As to the proportion of the peptide, radioactive iodine and chloramine T to be used, it is preferred to use about 1 mc of radioactive iodine and about 10 to 100 nano mols of chloramine T per nano mole of tyrosine molecule contained in the peptide where one radioactive iodine atom is introduced into tyrosine, and use about 2 mc of radioactive iodine and about 10–100 nano moles of chloramine T per nano mole of tyrosine molecule contained in the peptide where two iodine atoms are introduced into tyrosine. The thus-prepared radioiodinated peptide is isolated and purified by an ordinary separating means, e.g., extraction, distribution, column chromatography, dialysis, etc. The thus-obtained peptide can be stored, if necessary, by lyophilization.

For preparing the antibody by using the resulting antigen, the antigen is administered to a mammal in a conventional manner, and the antibody produced in vivo is collected. The mammal to be used for preparing the antibody is not particularly limited. However, rabbits and guinea pigs are usually desirable. In preparing the antibody, a predetermined amount of the antigen obtained as described above is diluted with a physiological saline solution to a predetermined concentration. This solution is then mixed with Freund's Complete Adjuvant to prepare a dispersion, which is then administered to the mammal. For example, the above-described dispersion is administered to a rabbit intradermally in a dosage of 0.5 to 5 mg of the antigen at a time. Thereafter, administration at a dosage of 0.5 to 5 mg is repeated once every two weeks for 2–10 months, preferably 4 to 6 months to immunize the rabbit.

Collection of the antibody may be performed by bleeding the immunized rabbit when a large amount of the antibody is prepared after the last administration of the dispersion containing the antigen, generally 1 to 2 weeks after the last administration, and centrifuging the blood thus-obtained to separate antiserum.

The process of the present invention has the advantage that a highly active and highly sensitive antibody can stably be obtained with good reproducibility which has an extremely excellent specificity to human and animal gut glucagon based on the uniqueness of the antigen used.

The thus obtained antibody has a particularly excellent specificity to gut glucagon as described above and enables one to assay human gut glucagon with high accuracy according to RIA method. This antibody can also be used for an enzyme immunoassay (EIA) method, a fluorescent immunoassay (FIA) method, etc. by labelling with an enzyme or a fluorescent material. Further, this antibody may be reacted with a known insolubilizing material to prepare an insoluble antibody.

This invention will be described in more detail by the following Reference Examples and Examples which, however, are not to be construed as limiting the present invention.

Additionally, $R_f$ values in Reference Examples were measured by thin layer chromatography on silica gel using the following mixed solvent:

$R_f{}^I$ . . . 1-butanol-acetic acid-water (4:1:5)
$R_f{}^{II}$ . . . 1-butanol-pyridine-acetic acid-water (31:20:6:24)

Preparation of the peptide of the general formula (1)

Reference Example 1

(1) Preparation of Z-ILe-Ala-OH:

10.87 g of Z-Ile-OSu dissolved in 50 ml of tetrahydrofuran was added to 30 ml of an aqueous solution containing 2.67 g of H-Ala-OH and 4.20 ml of triethylamine under ice-cooling. The reaction solution was stirred at room temperature for 20 hours followed by distilling off the solvent. Then, the residue was dissolved in 100 ml of a 2% triethylamine aqueous solution and washed three times with ethyl acetate. Upon acidifying the aqueous solution with 3 N-citric acid, an oily precipitate was formed, which was then extracted with ethyl acetate. The extract was then washed with 1 N-citric acid and saturated sodium chloride aqueous solution followed by distilling off the solvent. The residue was solidified from a methanol-ether mixed solution to obtain 6.5 g of end product. m.p. 156°–161° C.; $[\alpha]_D{}^{20}$: −29.4° C. (C=1.0; methanol)

(2) Preparation of Z-Asn-Ile-Ala-OH:

3.36 g of Z-Ile-Ala-OH was catalytically reduced in a mixed solvent of 20 ml of methanol and 15 ml of water in the presence of palladium black. The resulting dipeptide was dissolved in 20 ml of water containing 1.4 ml of triethylamine and 16 ml of tetrahydrofuran and cooled to −10° C. To this solution was added a mixed acid anhydride obtained from 3.46 g of Z-Asn-OH, 1.67 ml of isobutyl chloroformate and 1.42 ml of N-methylmorpholine at −10° C. in a mixed solution of 15 ml of dimethylformamide and 20 ml of tetrahydrofuran. The reaction mixture was stirred at 0° C. for 5 minutes, then at 15° C. for 30 minutes followed by distilling off the solvent. To the residue was added 1 N citric acid, and a precipitate thus-formed was washed with water, dried, and reprecipitated from methanol-ethyl acetate to purify. Thus, there was obtained 3.60 g of the end product. m.p. 240°–244° C. (d.); $[\alpha]_D{}^{19}$: −13.8° (C: 1.0; dimethylformamide)

(3) Preparation of Z-Asn-Asn-Ile-Ala-OH:

4.74 g of Z-Asn-Ile-Ala-OH was dissolved in 20 ml of glacial acetic acid. Then, 25 ml of 25% hydrogen bromide in acetic acid was added thereto and the mixture was allowed to stand at room temperature for 60 minutes. A precipitate formed by adding thereto anhydrous ether was collected by filtration, washed with ether, and dried over potassium hydroxide. The thus-obtained decarbobenzoxylated product was dissolved in 50 ml of dimethylformamide containing 3.08 ml of triethylamine and cooled to −10° C. To this solution was added a mixed acid anhydride of Z-Asn prepared from 4.18 g of Z-Asn-OH, 1.60 ml of N-methylmorpholine, and isobutyl chloroformate. Subsequent procedures were conducted in the same manner as in (2) described above to obtain 3.60 g of the end product. m.p. 235° C. (d.); $[\alpha]_D{}^{23}$: −10.1° (C: 0.5; 80% acetic acid)

(4) Preparation of Z-Lys(Tos)-Asn-Asn-Ile-Ala-OH 3.41 g of Z-Asn-Asn-Ile-Ala-OH was dissolved in 15 ml of glacial acetic acid, and 25 ml of 25% hydrogen bromide in acetic acid was added thereto to remove carbobenzoxy group as in (3) described above. The resulting decarbobenzoxylated product was dissolved in 30 ml of dimethylformamide containing 1.70 ml of triethylamine. To this solution was added a mixed acid anhydride obtained from 3.13 g of Z-Lys(Tos)-OH, 0.73 ml of N-methylmorpholine and 0.95 g of isobutyl chloroformate. Following the procedures described in (2), there was obtained 4.01 g of the end product. m.p. 229°–230° C. (d.); $[\alpha]_D{}^{23}$: −19.4° (C: 1.0; dimethylformamide).

(5) Preparation of Z-Arg-(NO$_2$)-Asn-Lys(Tos)-Asn-Asn-Ile-Ala-OH 2.03 g of Z-Lys(Tos)-Asn-Asn-Ile-Ala-OH was dissolved in 20 ml of glacial acetic acid. Then, 20 ml of 25% of hydrogen bromide-acetic acid was added thereto to remove the carbobenzoxy group as in (2) described above.

On the other hand, 4.19 g of Z-Arg(NO$_2$)-Asn-N$_2$H$_2$-Boc was left in trifluoroacetic acid for 30 minutes at room temperature to remove Boc, then dissolved in 20 ml of dimethylformamide. To this solution was successively added 3.61 ml of 6 N hydrochloric acid-dioxane and 0.96 ml of isoamyl nitrite at −15° C., and the resulting mixture was stirred at −10° C. for 5 minutes followed by adjusting pH to 7.5. This solution was added at −10° C. to 30 ml of the dimethylformamide solution containing the above-described decarbobenzoxylated product and 0.64 ml of triethylamine, and the reaction mixture was stirred at 4° C. for 20 hours followed by removing the solvent. To the residue was added 10% acetic acid, and the thus-solidified material was collected by filtration, washed with water, dried, and reprecipitated from methanol-ethyl acetate to obtain 2.19 g of the end product. m.p. 232°–234° C.; $[\alpha]_D^{21}$: −14.3° (C: 1.0; 80% acetic acid).

(6) Preparation of Z-Lys(Tos)-Arg-Asn-Lys(Tos)-Asn-Asn-Ile-Ala-OH 2.14 g of Z-Arg(NO$_2$)-Asn-Lys(Tos)-Asn-Asn-Ile-Ala-OH was catalytically reduced in 50 ml of 50% acetic acid in the presence of palladium black to remove the carbobenzoxy group. The resulting decarbobenzoxylated product was dissolved in 20 ml of dimethylformamide containing 2.52 ml of triethylamine. To this solution was added Z-Lys(Tos)-OSu prepared by reacting 2.40 g of Z-Lys(Tos)-OH with 0.64 g of N-hydroxysuccinimide in the presence of 1.14 g of dicyclohexylcarbodiimide without purification. The reaction mixture was stirred at room temperature for 20 hours followed by distilling off the solvent. To the residue was added 10% acetic acid to cause solidification. Thus, there was obtained 1.42 g of the end product. m.p. 200°–204° C.; $[\alpha]_D^{23}$: −30.5° (C: 1.0; 80% acetic acid).

(7) Preparation of Boc-Leu-Met-Asn-Thr-Lys(Tos)-Arg-Asn-Lys(Tos)-Asn-Asn-Ile-Ala-OH 1.38 g of Z-Lys(Tos)-Arg-Asn-Lys(Tos)-Asn-Asn-Ile-Ala-OH was dissolved in 5 ml of glacial acetic acid, and 7 ml of 25% hydrogen bromide-acetic acid was added thereto to remove the carbobenzoxy group as in (3) described above.

1.75 g of Boc-Leu-Met-Asn-ThrN$_2$H$_3$ was dissolved in 15 ml of dimethylformamide, and treated with 1.43 ml of 6 N hydrochloric acid-dioxane and 0.38 ml of isoamyl nitrite in the same manner as in (5), then added to 15 ml of dimethylformamide containing the above-described decarbobenzoxylated product and 0.28 ml of triethylamine. The reaction mixture was stirred at 4° C. for 20 hours followed by distilling off the solvent. The residue was subjected to a counter current distribution method in a 1-butanol-2% acetic acid system, and the 1-butanol layer was collected followed by distilling off the solvent. To the residue was added ethyl acetate, and the solidified product was washed with methanol to obtain 1.10 g of the end product. $R_f$ value: 0.28

(8) Preparation of Boc-Trp-Leu-Met-Asn-Thr-Lys(Tos)-Arg-Asn Lys(Tos)-Asn-Asn-Ile-Ala-OH 1.05 g of Boc-Leu-Met-Asn-Thr-Lys(Tos)-Arg-Asn-Lys(Tos)-Asn-Asn-Ile-Ala-OH was left in 6 ml of trifluoroacetic acid at room temperature for 30 minutes, and dry ether was added thereto. The precipitate thus-formed was collected by filtration, washed with ether and dried over potassium hydroxide under reduced pressure to obtain the Boc-free product.

Boc-Trp-OSu (prepared by reacting 700 mg of Boc-Trp-OH with 265 mg of N-hydroxysuccinimide under the action of 475 mg of dicyclohexylcarbodiimide) was dissolved in 20 ml of dioxane, and this solution was added to 15 ml of a dimethylformamide solution containing the above-described Boc-free product and 0.16 ml of triethylamine. This reaction mixture was stirred at room temperature for 24 hours followed by distilling off the solvent. To the residue was added ethyl acetate, and the thus solidified product was washed with ethanol to obtain 798 mg of the end product. $R_f$: 0.44.

(9) Preparation of Boc-Val-Gln-Trp-Leu-Met-Asn-Thr-Lys(Tos)-Arg-Asn-Lys(Tos)-Asn-Asn-Ile-Ala-OH 777 mg of Boc-Trp-Leu-Met-Asn-Thr-Lys(Tos)-Arg-Asn-Lys(Tos)-Asn-Asn-Ile-Ala-OH was treated in 4 ml of trifluoroacetic acid to remove Boc as in (8).

A solution of 513 mg of Boc-Val-Gln-OSu in 10 ml of dimethylformamide was added to a solution of the above-described Boc-free product and 0.02 ml of triethylamine in 5 ml of dimethylformamide. This reaction mixture was stirred at room temperature for 24 hours followed by distilling off the solvent. Then, 10% acetic acid was added to the residue, and the thus-solidified product was washed with water and ethanol to obtain 662 mg of the end product. $R_f$: 0.26.

(10) Preparation of H-Arg-Arg-Ala-Gln-Asp-Phe-Val-Gln-Trp-Leu-Met-Asn-Thr-Lys(Tos)-Arg-Asn-Lys(Tos)-Asn-Asn-Ile-Ala-OH 645 mg of Boc-Val-Gln-Trp-Leu-Met-Asn-Thr-Lys(Tos)-Arg-Asn-Lys(Tos)-Asn-Asn-Ile-Ala-OH was left at room temperature for 40 minutes in the presence of 4 ml of trifluoroacetic acid, 0.4 ml of ethanedithiol and 0.2 ml of anisole to remove Boc as in (8) described above.

783 mg of Boc-Arg-Arg-Ala-Gln-Asp-Phe-N$_2$H$_3$ (m.p. 158°–163° C.(d.)); $[\alpha]_D^{22}$: −1.0° (C: 1.0; dimethylsulfoxide) was dissolved in 10 ml of dimethylformamide and, after adding thereto 0.35 ml of 6 N-hydrochloric acid-dioxane at −15° C., 0.09 ml of isoamyl nitrite was further added thereto. After stirring the solution at −10° C. for 5 minutes, the pH of the solution was adjusted to 7.5 with triethylamine. The resulting solution was added to a solution of the above-described Boc-free product and 0.12 ml of triethylamine in 10 ml of dimethylformamide at −10° C. This reaction mixture was stirred at 4° C. for 20 hours followed by distilling off the solvent. The residue was then solidified by adding ethyl acetate, collected by filtration, and dried.

This reaction product was subjected, without further purification, to the step of removing Boc with 5 ml of trifluoroacetic acid in the presence of 0.5 ml of ethanedithiol. The resulting Boc-free product was dissolved in 20 ml of a mixed solution of 1-butanol-methanol-water (1:1:1) and the solution was charged on a column of Amberlite IRA-410 (2×4 cm) to convert the product to an acetate. The thus-obtained acetate was lyophilized, dissolved in 1 M acetic acid, placed on a Sephadex G25 column (3×190 cm), and subjected to gel filtration using 1 M acetic acid as an eluent. Fractions containing the end product (Nos. 64 to 80) were collected, and the solvent was distilled off followed by lyophilizing the residue. This was then dissolved in 5 ml of a lower layer of a partridge system (1-butanol:acetic acid:water=4:1:5), and purified by a liquid drop counter current distribution method using an upper layer of the same solvent system. Fractions containing the end product were collected, and the solvent was distilled off followed by conducting lyophilization to obtain 260 mg of the end product. $R_f^I$: 0.20; $R_f^{II}$: 0.65.

Amino acid analysis of acid-decomposed product:
Lys (2) 2.11, Arg (3) 2.60, Asp (5) 4.74, Thr (1) 0.87, Glu (2) 2.08, Ala (2) 2.17, Val (1) 1.18, Met (1) 1.03, Ile (1) 0.95, Leu (1) 1.02, Phe (1) 1.06.

(11) Preparation of H-Ser-Lys(Tos)-Tyr-Leu-Asp-Ser-Arg-Arg-Ala-Gln-Asp-Phe-Val-Gln-Trp-Leu-Met-Asn-Thr-Lys(Tos)-Arg-Asn-Lys(Tos)-Asn-Asn-Ile-Ala-OH 485 mg of Boc-Ser-Lys(Tos)-Tyr-Leu-Asp-Ser-N$_2$H$_3$ (m.p. 174°–175° C. (d.)); $[\alpha]_D^{22}$: −21.8° (C: 1.0; dimethylformamide)) was condensed with H-Arg-Arg-Ala-Gln-Asp-Phe-Val-Gln-Trp-Leu-Met-Asn-Thr-Lys(Tos)-Arg-Asn-Lys(Tos)-Asn-Asn-Ile-Ala-OH according to an azide method using 0.15 ml of 6 N-hydrochloric acid-dioxane and 0.31 ml of 20% isoamyl nitritedimethylformamide solution in the same manner as in (10) above. After completion of the reaction, the solvent was distilled off. Upon adding thereto ethyl acetate, it solidified. This crude product was dissolved in 5 ml of a lower layer of partridge sysem (1-butanol:acetic acid:water=4:1:5), and subjected to a liquid drop counter current distribution method to conduct purification. Fractions containing the end product were collected, and the solvent was distilled off. The residue was dissolved in 7 ml of a mixed solution of 1-butanol-methanol-water (1:1:1), and placed on a column of Sephadex LH 20 (3×108 cm) to conduct gel filtration using 1-butanol-methanol-water (1:1:1) as an eluent. Fractions containing the end product were collected, and the solvent was distilled off. To the residue was then added ethyl acetate to cause solidification. The thus-solidified product was treated in the presence of 3 ml of trifluoroacetic acid and 0.2 ml of ethanedithiol to remove Boc. The dried Boc-free product was dissolved in 5 ml of 1 M acetic acid, and placed on a column of Sephadex G50 (3×145 cm) to conduct gel filtration using 1 M acetic acid as an eluent. Fractions containing the end product (Nos. 43–57) were collected followed by distilling off the solvent. The residue was then lyophilized to obtain 93 mg of the end product. $R_f^I$: 0.25; $R_f^{II}$: 0.54

Amino acid analysis of acid-decomposed product (6 N HCl; 110° C.; 24 hrs):

Lys (3) 2.80, Arg (3) 2.89, Asp (6) 6.10 Thr (1) 0.97, Ser (2) 1.79, Glu (2) 2.06, Ala (2) 2.03, Val (1) 0.99, Met (1) 0.87, Ile (1) 1.00, Leu (2) 1.98, Thr (1) 1.00, Phe (1) 1.00.

(12) Preparation of H-Lys-Arg-Asn-Lys-Asn-Asn-Ile-Ala-OH 25 mg of Z-Lys(Tos)-Arg-Asn-Lys(Tos)-Asn-Asn-Ile-Ala-OH was dissolved in 30 ml of liquid ammonia, and metallic sodium was added thereto in small pieces. When the reaction solution appeared blue, 0.5 g of dry ammonium chloride was added thereto followed by distilling off ammonia. The residue was dissolved in 1 M acetic acid and subjected to gel filtration using Sephadex G10 (4×43 cm) using 1 M acetic acid as eluent. Fractions containing the end product were collected, and the solvent was distilled off followed by lyophilizing the residue to obtain 10 mg of the end product. $R_f^I$: 0.01; $R_f^{II}$: 0.27

Amino acid analysis of acid-decomposed product:

Lys (2) 1.84, Arg (1) 0.94, Asp (3) 3.08, Ala (1) 1.08, Ile (1) 1.05

(13) Preparation of H-Val-Gln-Trp-Leu-Met-Asn-Thr-Lys-Arg-Asn-Lys-Asn-Asn-Ile-Ala-OH 10 mg of Boc-Val-Gln-Trp-Leu-Met-Asn-Thr-Lys(-Tos)-Arg-Asn-Lys(Tos)-Asn-Asn-Ile-Ala-OH was treated in the presence of 1 ml of trifluoroacetic acid and 0.1 ml of ethanedithiol to remove Boc, then treated with metallic sodium in liquid ammonia in the same manner as in (12) above to remove the protective groups. Purification by gel filtration yielded 5 mg of the end product. $R_f^I$: 0.20; $R_f^{II}$: 0.49; $[\alpha]_D^{23}$: −50.0 (C: 0.07; 1 M acetic acid).

(14) Preparation of H-Arg-Arg-Ala-Gln-Asp-Phe-Val-Gln-Trp-Leu-Met-Asn-Thr-Lys-Arg-Asn-Lys-Asn-Asn-Ile-Ala-OH 100 mg of H-Arg-Arg-Ala-Gln-Asp-Phe-Val-Gln-Trp-Leu-Met-Asn-Thr-Lys(Tos)-Arg-Asn-Lys(Tos)-Asn-Asn-Ile-Ala-OH was treated in the same manner as in (12) above to remove all protective groups. Purification by gel filtration gave 40 mg of the end product. $R_f^I$: 0.20; $R_f^{II}$: 0.51; $[\alpha]_D^{23}$: −46.3°. (C: 0.2; 1 M acetic acid)

(15) Preparation of H-Ser-Lys-Tyr-Leu-Asp-Ser-Arg-Arg-Ala-Gln-Asp-Phe-Val-Gln-Trp-Leu-Met-Asn-Thr-Lys-Arg-Asn-Lys-Asn-Asn-Ile-Ala-OH.

10 mg of H-Ser-Lys(Tos)-Tyr-Leu-Asp-Ser-Arg-Arg-Ala-Gln-Asp-Phe-Val-Gln-Trp-Leu-Met-Asn-Thr-Lys(Tos)-Arg-Asn-Lys(Tos)-Asn-Asn-Ile-Ala-OH was treated in the same manner as in (12) above to remove all protective groups, then subjected to gel filtration on Sephadex G-50 (2.5×135 cm) using 1 M acetic acid as an eluent. Fractions containing the end product were collected and lyophilized to obtain 4 mg of the end product. $R_f^I$: 0.20; $R_f^{II}$: 0.49; $[\alpha]_D^{23}$: −60.9° (C: 0.1; 1 M acetic acid)

[Preparation of antibody]

EXAMPLE 1

10 mg of the peptide obtained in Reference Example 1 (14) (hereinafter referred to simply as "Peptide A" for brevity) and 5 mg of bovine serum albumin (hereinafter referred to simply as "BSA" for brevity) were dissolved in 2 ml of an ammonium acetate buffer solution (0.1 M; pH 7.0), and 0.11 ml of a 0.1 M glutaraldehyde solution was added thereto followed by stirring at room temperature for 5 hours. The reaction mixture was then dialyzed for 48 hours at 4° C. using 1 liter of water during which the water was exchanged 5 times. The resulting solution containing peptide-protein complex was then lyophilized to obtain 14 mg of the gut glucagon antigen (hereinafter referred to simply as "Antigen I" for brevity).

Antigen I thus-obtained was further subjected to gel filtration using Sephadex G-50 (eluent: physiological saline solution; detection: OD 280 mm; eluting rate: 3 ml/hr; dispensed amount: 1 ml portion). Fraction [I] containing Peptide A bound to BSA was separated from Fraction [II] containing other product (dimer of Peptide A), and Fraction [I] was dialyzed against 0.6% sodium chloride aqueous solution at 4° C. for 24 hours and lyophilized to obtain 7 mg of white, powdery Peptide A-BSA complex (hereinafter referred to simply as "Antigen I'" for brevity). This complex was a complex of 1 mole of BSA with on the average 13 moles of Peptide A coupled thereto. Additionally, this binding ratio was obtained as follows.

That is, at first a standard curve for the concentration of the Peptide A dimer was prepared based on the fact that unreacted BSA and Peptide A were not found to remain, and the amount of the Peptide A dimer in the above fraction was calculated from the standard curve. Then, the amount was deducted from the amount of initially charged Peptide A. The resulting amount of Peptide A was assumed to correspond to the amount of Peptide A coupled to BSA.

EXAMPLE 2

5 mg of the peptide, H-Leu-Met-Asn-Thr-Lys-Arg-Asn-Lys-Asn-Asn-Ile-Ala-OH, obtained in the same manner as in Reference Example 1 (hereinafter referred to simply as "Peptide B" for brevity) and 5 mg of BSA were dissolved in 2 ml of an ammonium acetate buffer (0.1 M; pH 7.0). 0.11 ml of a 0.1 M glutaraldehyde solution was added to this solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 9 mg of a gut glucagon antigen (hereinafter referred to simply as "Antigen II" for brevity).

This Antigen II was further subjected to gel filtration using Sephadex G-50 to separate Fraction [I] containing Peptide B coupled to BSA from Fraction [II] containing other product (Peptide B dimer), and Fraction [I] was dialyzed against 0.6% saline solution at 4° C. for 24 hours and lyophilized to obtain 6 mg of white, powdery Peptide B-BSA complex. This complex was a complex of 1 mole of BSA with on the average 10 moles of Peptide B coupled thereto.

EXAMPLE 3

4 mg of the peptide obtained in Reference Example 1 (12) (hereinafter referred to simply as "Peptide C" for brevity) and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 7.5 mg of a gut glucagon antigen (hereinafter referred to simply as "Antigen III" for brevity).

This Antigen III was further subjected to gel filtration using Sephadex G-50 to separate Fraction [I] containing Peptide C coupled to BSA from Fraction [II] containing other product (Peptide C dimer), and Fraction [I] was dialyzed against 0.6% saline solution at 4° C. for 24 hours and lyophilized to obtain 5.5 mg of white, powdery Peptide C-BSA complex. This complex was a complex of 1 mole of BSA with on the average 8 moles of Peptide C coupled thereto.

EXAMPLE 4

4 mg of the Peptide, H-Lys-Lys-Arg-Asn-Lys-Asn-Asn-Ile-Ala-OH, obtained as in Reference Example 1 (hereinafter abbreviated as "Peptide D") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 8 mg of a gut glucagon antigen (hereinafter abbreviated as "Antigen IV").

This Antigen IV was further subjected to gel filtration using Sephadex G-50 to separate Fraction [I] containing Peptide D bound to BSA and Fraction [II] containing other product (Peptide D dimer), and Fraction [I] was dialyzed against 0.6% saline solution at 4° C. for 24 hours and lyophilized to obtain 6 mg of white powdery Peptide D-BSA complex. This complex was a complex of 1 mole of BSA with on the average 9 moles of Peptide D coupled thereto.

EXAMPLE 5

4 mg of the Peptide, H-Tyr-Lys-Arg-Asn-Lys-Asn-Asn-Ile-Ala-OH, obtained as in Reference Example 1 (hereinafter abbreviated as "Peptide E") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 7 mg of a gut glucagon antigen (hereinafter abbreviated as "Antigen V").

This Antigen V was further subjected to gel filtration using Sephadex G-50 to separate Fraction [I] containing Peptide E bound to BSA and Fraction [II] containing other product (Peptide E dimer), and Fraction [I] was dialyzed against 0.6% saline solution at 4° C. for 24 hours and lyophylized to obtain 5 mg of white, powdery Peptide E-BSA complex. This complex was a complex of 1 mole of BSA with on the average 6 moles of Peptide E coupled thereto.

EXAMPLE 6

5 mg of the peptide, H-Gly-Lys-Lys-Arg-Asn-Lys-Asn-Asn-Ile-Ala-OH, obtained as in Reference Example 1 (hereinafter abbreviated as "Peptide F") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 9 mg of a gut glucagon antigen (hereinafter abbreviated as "Antigen VI").

This Antigen VI was further subjected to gel filtration using Sephadex G-50 to separate Fraction [I] containing Peptide F found to BSA and Fraction [II] containing other product (Peptide F dimer), and Fraction [I] was dialyzed against 0.6% saline solution at 4° C. for 24 hours and lyophilized to obtain 6 mg of white, powdery Peptide F-BSA complex. This complex was a complex of 1 mole of BSA with on the average 14 moles of Peptide F coupled thereto.

EXAMPLE 7

4 mg of the peptide, H-Ala-Lys-Arg-Asn-Lys-Asn-Asn-Ile-Ala-OH, obtained as in Reference Example 1 (hereinafter abbreviated as "Peptide G") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 7.5 mg of a gut glucagon antigen (hereinafter abbreviated as "Antigen VII").

This Antigen VII was further subjected to gel filtration using Sephadex G-50 to separate Fraction [I] containing Peptide G bound to BSA and Fraction [II] containing other product (Peptide G dimer), and Fraction [I] was dialyzed against 0.6% saline solution at 4° C. for 24 hours and lyophilized to obtain 5.5 mg of white, powdery Peptide G-BSA complex. This complex was a complex of 1 mole of BSA with on the average 9 moles of Peptide G coupled thereto.

EXAMPLE 8

4 mg of the peptide, H-Gly-Lys-Arg-Asn-Lys-Asn-Asn-ILe-Ala-OH, obtained as in Reference Example 1 (hereinafter abbreviated as "Peptide H") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 7.5 mg of a gut glucagon antigen (hereinafter abbreviated as "Antigen VIII").

This Antigen VIII was further subjected to gel filtration using Sephadex G-50 to separate Fraction [I] containing Peptide H bound to BSA and Fraction [II] containing other product (Peptide H dimer), and Fraction [I] was dialyzed against 0.6% saline solution at 4° C. for 24 hours and lyophilized to obtain 6 mg of white, powdery Peptide H-BSA complex. This complex was a complex of 1 mole of BSA with on the average 10 moles Peptide H coupled thereto.

EXAMPLE 9

12 mg of the peptide obtained in Reference Example 1 (15) (hereinafter abbreviated as "Peptide I") and 5 mg of BSA were dissolved in 2 ml of an ammonium acetate buffer solution (0.1 M; pH 7.0). To this solution was added 0.11 ml of a 0.1 M glutaraldehyde solution followed by stirring at room temperature for 5 hours. The reaction mixture was then dialyzed against 1 liter of water at 4° C. for 48 hours during which the water was exchanged 5 times. The resulting solution containing peptide-protein complex was lyophilized to obtain 15 mg of a gut glucagon antigen (hereinafter abbreviated as "Antigen IX").

This Antigen IX was further subjected to gel filtration using Sephadex G-50 to separate Fraction [I] containing Peptide I bound to BSA and Fraction [II] containing other product (Peptide I dimer), and Fraction [I] was dialyzed against 0.6% saline solution at 4° C. for 24 hours and lyophilized to obtain 7.5 mg of white, powdery Peptide K-BSA complex. This complex was a complex of 1 mole of BSA with on the average 10 moles of Peptide I coupled thereto.

[Preparation of antibody]

EXAMPLE 10

3 mg of Antigen I obtained in Example 1 was dissolved in 1.5 ml of physiological saline solution and 1.5 ml of Freund's Complete Adjuvant was added thereto to form a dispersion. The dispersion thus obtained was administered intradermally to three rabbits (weighing 2.5 to 3.0 Kg). Thereafter, administration at the same dosage was repeated 5 times once every two weeks. Further, administration at the dosage half of the initial dosage was repeated 5 times once every month. Ten days after the final administration, the immunized animals were bled, and the blood thus-obtained was centrifuged to separate antiserum. Thus, there was obtained a gut glucagon antibody of the present invention (hereinafter abbreviated as "Antibody I").

EXAMPLE 11

3 mg of Antigen I' obtained in Example 1 was dissolved in 1.5 ml of a physiological saline solution and 1.5 ml of Freund's Complete Adjuvant was added thereto to form a dispersion. The dispersion thus-obtained was administered intradermally to three rabbits (weighing 2.5 to 3.0 Kg). Thereafter, administered at the same dosage was repeated 5 times once every two weeks. Further, administration at the dosage half of the initial dosage was repeated 5 times once every month. Ten days after the final administration, the immunized animals were bled, and the blood thus-obtained was centrifuged to separate antiserum. Thus, there was obtained a gut glucagon antibody of the present invention (hereinafter abbreviated as "Antibody II").

EXAMPLE 12

3 mg of Antigen IX obtained in Example 9 was dissolved in 1.5 ml of a physiological saline solution and 1.5 ml of Freund's Complete Adjuvant was added thereto to form a dispersion. The dispersion thus-obtained was administered intradermally to three rabbits (weighing 2.5 to 3.0 Kg). Thereafter, administration at the same dosage was repeated 5 times once every two weeks. Further, administration at the dosage half of the initial dosage was repeated 5 times once every month. Ten days after the final administration, the immunized animals were bled, and the blood thus-obtained was centrifuged to separate antiserum. Thus, there was obtained a gut glucagon antibody of the present invention (hereinafter abbreviated as "Antibody III").

EXAMPLE 13

3 mg of Antigen II obtained in Example 2 was dissolved in 1.5 ml of a physiological saline solution and 1.5 ml of Freund's Complete Adjuvant was added thereto to form a dispersion. The dispersion thus-obtained was administered intradermally to three rabbits (weighing 2.5 to 3.0 Kg). Thereafter, administration at the same dosage was repeated 5 times once every two weeks. Further administration at the dosage half of the initial dosage was repeated 5 times once every month. Ten days after the final administration, the immunized animals were bled, and the blood thus-obtained was centrifuged to separate antiserum. Thus, there was obtained a gut glucagon antibody of the present invention (hereinafter abbreviated as "Antibody IV").

EXAMPLE 14

3 mg of Antigen III obtained in Example 3 was dissolved in 1.5 ml of a physiological saline solution and 1.5 ml of Freund's Complete Adjuvant was added thereto to form a dispersion. The dispersion thus obtained was administered intradermally to three rabbits (weighing 2.5 to 3.0 Kg). Thereafter, administration at the same dosage was repeated 5 times once every two weeks. Further, administration at the dosage half of the initial dosage was repeated 5 times once every month. Ten days after the final administration, the immunized animals were bled, and the blood thus-obtained was centrifuged to separate antiserum. Thus, there was obtained a gut glucagon antibody of the present invention (hereinafter abbreviated as "Antibody V").

EXAMPLE 15

When the antigens obtained in Examples 4 to 8 were used and treated in the same manner as in Example 10, there were obtained antibodies with high activity and high specificity to gut glucagon.

REFERENCE EXAMPLE 2

Preparation of labelled peptide: H-Ser-Lys-Tyr-Leu-Asp-Ser-Arg-Arg-Ala-Gln-Asp-Phe-Val-Gln-Trp-Leu-Met-Asn-Thr-Lys-Arg-Asn-Lys-Asn-Asn-Ile-Ala-OH was labelled by the process of using chloramine T. That is, 10 μl of an aqueous solution containing 5 mg of the above-described peptide and 10 μl of an aqueous solution containing 1 mc of [$^{125}$I]Na(MEN) and 20 μg of chloramine T were gradually added to 20 μl of a 1.0 M phosphate buffer solution (pH 7.4). After 30 seconds, the reaction was discontinued by adding thereto a 50 μl aqueous solution containing 100 μg of sodium metadisulfate. The reaction mixture was then placed on a column of Sephadex G-10 (1.0×30 cm) using 0.1 M acetic acid as an eluent. The eluant was collected by 1 ml portions, and fractions No. 8 to 11 were collected to obtain a solution containing H-Ser-Lys-[$^{125}$I-monoiodo-Tyr]-Leu-Asp-Ser-Arg-Arg-Ala-Gln-Asp-Phe-Val-Gln-Trp-Leu-Met-Asn-Thr-Arg-Asn-Lys-Asn-Asn-Ile-Ala-OH.

Antibody Activity Determination

Activity of each of the thus-obtained antibodies was determined as follows. That is, each of the antibodies was initially diluted with a physiological saline solution to concentrations of $10^{-1}, 10^{-2}, 10^{-3}, 10^{-4}, 10^{-5}, \ldots$. To 100 μl of each diluted solution were added 100 μl of $^{125}$I-labelled peptide (prepared by diluting the above-described solution to the degree of about 10,000 cpm) and 400 μl of a 0.05 M phosphate buffer (pH=7.5) [containing 0.25% BSA, 0.01 M EDTA and Trasylol (500 KIV/ml)], and the mixture was incubated at 4° C. for 66 hours. The resulting complex of the antibody and $^{125}$I-labelled antigen was separated from unreacted or free $^{125}$I-labelled peptide using dextran-coated activated carbon and centrifugation at 4° C. at a speed of 3,000 rpm for 15 minutes. Radioactivity of the complex thus obtained was counted to determine the binding ratio (%) of $^{125}$I-labelled peptide and antibody at each concentration. The binding ratio at each concentration was plotted, with binding ratio as ordinate and initial dilution of antibody as abscissa. The degree of dilution of antibody at which the binding ratio (%) is 50% was as follows.

| Antibody | Activity |
|---|---|
| Antibody I | 20000 |
| Antibody II | 25000 |
| Antibody III | 25000 |
| Antibody IV | 10000 |
| Antibody V | 5000 |

Gut Glucagon Specificity Determination

Pancreatic glucagon, the 80-100 peptide sequence of porcine glicentin and gut glucagon (Peak I described in Kenny J., *J. Clin. Endocr.*, 15, 865 (1955)) were used at various concentrations as test samples. And, as a standard diluent, a 0.05 M phosphate-physiological saline solution (pH 7.5) containing 0.25% BSA, 0.01 M EDTA, Trasylol (500 KIV/ml) and 0.01% NaN$_3$ was used.

400 μl of the standard diluent, 100 μl of each test sample, 100 ml of Antibody I obtained in Example 10 (activity: 20000) and 100 μl of $^{125}$I-labelled peptide (prepared by diluting the labelled peptide obtained above to the degree of about 10000 ppm) were placed in a test tube and incubated at 4° C. for 66 hours. To the mixture was added 1 ml of a dispersion of 0.25% activated carbon coated with 0.025% dextran followed by incubating at 4° C. for 30 minutes. The thus-treated mixture was separated into antibody-bound $^{125}$I-labelled standard peptide and unreacted (or free) labelled standard peptide by centrifugation at a speed of 3000 rpm at 4° C. The radioactivity of each peptide was measured. The binding ratio (%) of $^{125}$I-labelled peptide and each sample at each concentrated and dilution was determined taking binding ratio ($B_o$) corresponding to the activity of used antibody as 100%. The results thus-obtained are shown in FIG. 1. In FIG. 1, the ordinate represents the binding ratio (%) (B/Bo×100) and the abscissa represents the concentration of test sample (pancreatic glucagon and the 80-100 peptide sequence of porcine glicentin) and degree of dilution of gut glucagon (Peak I). In FIG. 1, letter (a) denotes pancreatic glucagon, letter (b) denotes the 80-100 peptide sequence of porcine glicentin, and letter (c) denotes gut glucagon.

From FIG. 1, it can be seen that Antibody I showed a curve representing reactivity with pancreatic glucagon which is clearly distinguishable from the curve representing reactivity with gut glucagon. From this, it follows that the antibody of this invention does not cross react with pancreatic glucagon and has excellent specificity.

Figure 2:
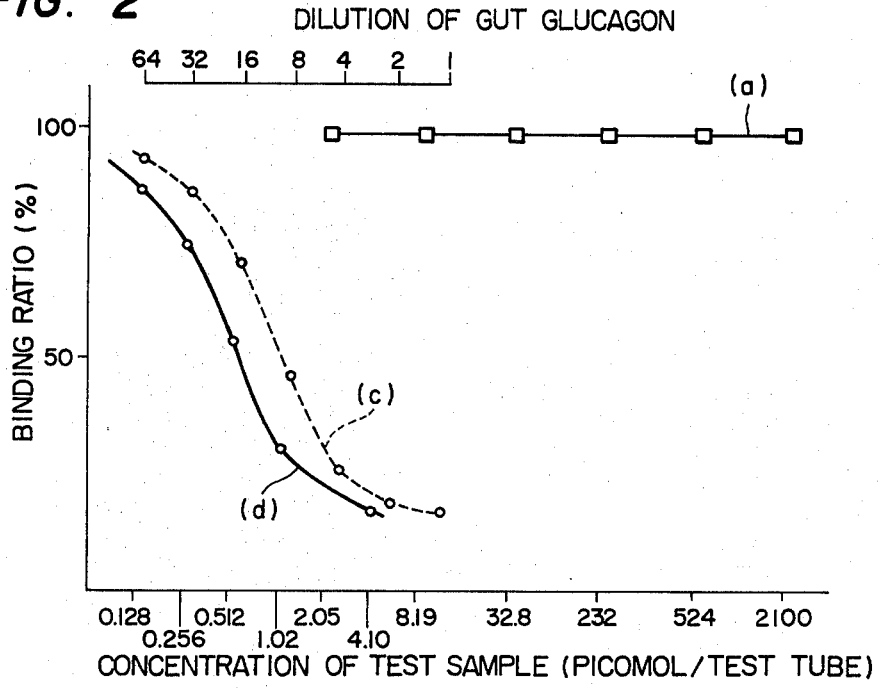

With Antibodies III, IV and V, the gut glucagon specificity was determined in the same manner as described above, and the results thus-obtained are shown in FIGS. 2, 3 and 4.

FIG. 2 is a graph showing specificity of Antibody III, wherein the ordinate represents the binding ratio (%) (B/Bo×100) and the abscissa represents the concentration of test sample (pancreatic glucagon and the 74-100 peptide sequence of porcine glicentin) and the degree of dilution of gut glucagon (Peak I). In FIG. 2, letter (a) denotes pancreatic glucagon, letter (c) denotes gut glucagon, and letter (d) denotes the 74-100 peptide sequence of porcine glicentin.

FIG. 3 is a graph showing specificity of Antigen IV, wherein the ordinate represents the binding ratio (%) (B/Bo×100) and the abscissa represents the concentration of test sample (pancreatic glucagon and the 89-100 peptide sequence of porcine glicentin) and the degree of dilution of gut glucagon (Peak I). In FIG. 3, letter (a) denotes pancreatic glucagon, letter (c) denotes gut glucagon, and the letter (e) denotes the 89-100 peptide sequence of porcine glicentin.

FIG. 4 is a graph showing specificity of Antibody V, wherein the ordinate represents the binding ratio (%) (B/Bo×100) and the abscissa represents the concentration of test sample (pancreatic glucagon and the 93-100 peptide sequence of porcine glicentin) and the degree of dilution of gut glucagon (Peak I). In FIG. 4, letter (a) denotes pancreatic glucagon, letter (c) denotes gut glucagon, and letter (f) denotes the 93-100 peptide sequence of porcine glicentin.

From FIGS. 2 to 4, it can be seen that all of Antibodies III, IV and V showed curves representing reactivity with pancreatic glucagon which are clearly distinguishable from curves representing reactivity with gut glucagon. From this, it follows that the antibodies of this invention do not crossreact with pancreatic glucagon and have excellent specificity to gut glucagon.

While the invention has been described in detail and with reference to specific embodiments thereof, it will be apparent to one skilled in the art that various changes and modifications can be made therein without departing from the spirit and scope thereof.

What is claimed is:

1. A gut glucagon-specific antibody prepared by administering to a mammal an antigen composed of a peptide-carrier complex obtained by (a) reacting a peptide as a hapten with a carrier in the presence of a binding agent for binding the hapten and the carrier to each other, and
(b) collecting the resulting antibody, wherein the peptide is represented by the general formula:

R-Lys-Arg-Asn-Lys-Asn-Asn-Ile-Ala-OH wherein R represents a member selected from the group consisting of H, H-Arg-, H-Trp-, H-Asn-, H-Ala, H-Val-, H-Met, H-Leu-, H-Phe-, H-Lys-, H-Thr-, H-Ile-,

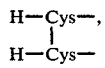

H-Gly-, H-His-, H-Pro-, H-Cys, H-Gly-Lys-, H-Asn-Tyr-, H-Met-Thr-, H-Met-Asn-, H-Leu-Thr-, H-Trp-Thr-, H-Phe-Val-, H-Gln-Ala-, H-Asp-Arg-, H-Leu-Tyr-, H-Ser-Lys-, H-Met-Asn-Thr-, H-Leu-Met-Asn-Thr-, H-Trp-Leu-Met-Asn-Thr-, H-Gln-Trp-Leu-Met-Asn-Thr-, H-Val-Gln-Trp-Leu-Met-Asn-Thr-, H-Phe-Val-Gln-Trp-Leu-Met-Asn-Thr-, H-Asp-Phe-Val-Gln-Trp-Leu-Met-Asn-Thr-, H-Gln-Asp-Phe-Val-Gln-Trp-Leu-Met-Asn-Thr-, H-Ala-Gln-Asp-Phe-Val-Gln-Trp-Leu-Met-Asn-Thr-, H-Arg-Ala-Gln-Asp-Phe-Val-Gln-Trp-Leu-Met-Asn-Thr-, H-Arg-Arg-Ala-Gln-Asp-Phe-Val-Gln-Trp-Leu-Met-Asn-Thr-, H-Ser-Arg-Arg-Ala-Gln-Asp-Phe-Val-Gln-Trp-Leu-Met-Asn-Thr-, H-Asp-Ser-Arg-Arg-Ala-Gln-Asp-Phe-Val-Gln-Trp-Leu-Met-Asn-Thr-, H-Leu-Asp-Ser-Arg-Arg-Ala-Gln-Asp-Phe-Val-Gln-Trp-Leu-Met-Asn-Thr-, H-Tyr-Leu-Asp-Ser-Arg-Arg-Ala-Gln-Asp-Phe-Val-Gln-Trp-Leu-Met-Asn-Thr-, H-Lys-Tyr-Leu-Asp-Ser-Arg-Arg-Ala-Gln-Asp-Phe-Val-Gln-Trp-Leu-Met-Asn-Thr-, and H-Ser-Lys-Tyr-Leu-Asp-Ser-Arg-Arg-Ala-Gln-Asp-Phe-Val-Gln-Trp-Leu-Met-Asn-Thr-.

2. The antibody as claimed in claim 1, wherein said carrier is a member selected from the group consisting of animal serum albumins, animal serum globulins, animal thyroglobulins, animal hemoglobins, animal hemocyanins, protein extract from ascaris, polylysine, polyglutamic acid, lysine-glutamic acid copolymer, lysine-containing copolymer, and ornithine-containing copolymer.

3. The antibody as claimed in claim 1, wherein said binding agent is a member selected from the group consisting of glyoxal, malondialdehyde, glutaraldehyde, succinaldehyde, adipoaldehyde, N-N'-o-phenylenedimaleimide, N,N'-m-phenylenediamaleimide, m-maleimidobenzoyl-N-hydroxysuccinimide ester, 4-(maleimidemethyl)-cyclohexane-1-carboxyl-N'-hydroxy-succinimide ester, N,N'-dicyclohexyl carbodiimide, N-ethyl-N'-dimethylaminocarbodiimide, 1-ethyl-3-diisopropylamino carbodiimide, 1-cyclohexyl-3-(2-morpholinyl-4-ethyl)-carbodiimide, and p-diazoniumphenylacetic acid.

4. The antibody as claimed in claim 1, wherein R represents a member selected from the group consisting of H, H-Gly-, H-Ala-, H-Tyr-, H-Lys-, H-Gly-Lys-, H-Leu-Met-Asn-Thr-, H-Val-Gln-Trp-Leu-Met-Asn-Thr-, H-Arg-Arg-Ala-Gln-Asp-Phe-Val-Gln-Trp-Leu-Met-Asn-Thr-, and H-Ser-Lys-Tyr-Leu-Asp-Ser-Arg-Arg-Ala-Gln-Asp-Phe-Val-Gln-Trp-Leu-Met-Asn-Thr-.

5. The antibody as claimed in claim 4, wherein R represents H-Arg-Arg-Ala-Gln-Asp-Phe-Val-Gln-Trp-Leu-Met-Asn-Thr-, said carrier is bovine serum albumin and said binding agent is glutaraldehyde.

6. The antibody as claimed in claim 4, wherein R represents H-Ser-Lys-Thr-Leu-Asp-Ser-Arg-Arg-Ala-Gln-Asp-Phe-Val-Gln-Trp-Leu-Met-Asn-Thr-, said carrier is bovine serum albumin and said binding agent is glutaraldehyde.

7. The antibody as claimed in claim 4, wherein R represents H-Leu-Met-Asn-Thr-, said carrier is bovine serum albumin and said binding agent is glutaraldehyde.

8. The antibody as claimed in claim 4, wherein R represents a hydrogen atom, said carrier is bovine serum albumin and said binding agent is glutaraldehyde.

* * * * *